United States Patent [19]

Koga et al.

[11] Patent Number: 4,878,921
[45] Date of Patent: Nov. 7, 1989

[54] NATURAL BLUE DYE COMPOSITION AND COLORANT USING THE SAME: PREPARED BY REACTING TAURINE AND GENIPIN

[75] Inventors: Kunimasa Koga; Shigeaki Fujikawa; Yuko Fukui, all of Osaka, Japan

[73] Assignee: Suntory Limited, Osaka, Japan

[21] Appl. No.: 65,033

[22] Filed: Jun. 19, 1987

[30] Foreign Application Priority Data

Jun. 21, 1986 [JP] Japan .................................. 61-145651

[51] Int. Cl.$^4$ ......................... A23L 1/27; C09B 61/00
[52] U.S. Cl. ........................................ 8/646; 8/438; 8/591; 8/602
[58] Field of Search ............................................ 8/646

[56] References Cited

FOREIGN PATENT DOCUMENTS 52-053934 4/1977 Japan .
57-081466 5/1982 Japan .
61-047167 3/1986 Japan .

Primary Examiner—A. Lionel Clingman
Attorney, Agent, or Firm—Cushman, Darby & Cushman

[57] ABSTRACT

A natural blue dye composition that has improved stability and which can be used as a colorant in a broad range of applications including foodstuffs and drugs, and a process for preparing the same are disclosed.

Genipin which is derived from gardenia fruit by hydrolysis of iridoid glycoside geniposide under action of β-glucosidase, is reacted with taurine to produce a stable blue dye compositions.

5 Claims, 2 Drawing Sheets

NATURAL BLUE DYE COMPOSITION AND COLORANT USING THE SAME: PREPARED BY REACTING TAURINE AND GENIPIN

BACKGROUND OF THE INVENTION

The present invention relates to a natural blue dye composition and a colorant what utilizes the same.

With growing concern over the safety of synthetic dyes, the importance of natural dyes suitable for use in foods has gained increasing acceptance. The only natural blue dyes commercially feasible today are those derived from gardenia and algae Spirulina. However, there is a problem associated with the stability of these dyes and the development of natural blue dyes exhibiting good stability is desired.

The present invention provides a natural blue dye composition that has improved stability and which can be used as a colorant in a broad range of applications including foodstuffs and drugs.

Japanese Patent Public Disclosure Nos. 13451/1979 and 92792/1981 disclose a gardenia derived blue dye that is obtained by a process comprising hydrolyzing the iridoid glycoside geniposide from the fruit of gardenia under action of β-glucosidase and reacting the resulting genipin with a primary amino containing compound such as amine or amino acid. However, this dye is not stable in solution, particularly in the face of changes in pH, and its use in acidic foods has been sometimes limited.

Phycocyanin derived from algae Spirulina is a protein dye, so it is very poor in stability in ethanol containing aqueous solutions and cannot be used as a colorant in alcoholic beverages.

SUMMARY OF THE INVENTION

An object, therefore, of the present invention is to produce a blue dye composition from the gardenia fruit derived genipin, that is stable over a broad pH range and in an ethanol-containing aqueous solution and which affords a brilliant color as manifested by a narrow half-width in visible absorption spectrum.

With a view to solving the aforementioned problems of the prior art, the present inventors conducted intensive studies and, to their great surprise, it was found that when taurine which is a kind of aminosulfonic acid was used as the primary amino containing compound to be reacted with the gardenia fruit derived genipin, the blue dye composition obtained as the reaction product exhibited far better stability than the known gardenia derived blue dyes.

DETAILED DESCRIPTION OF THE INVENTION

Figure 1:
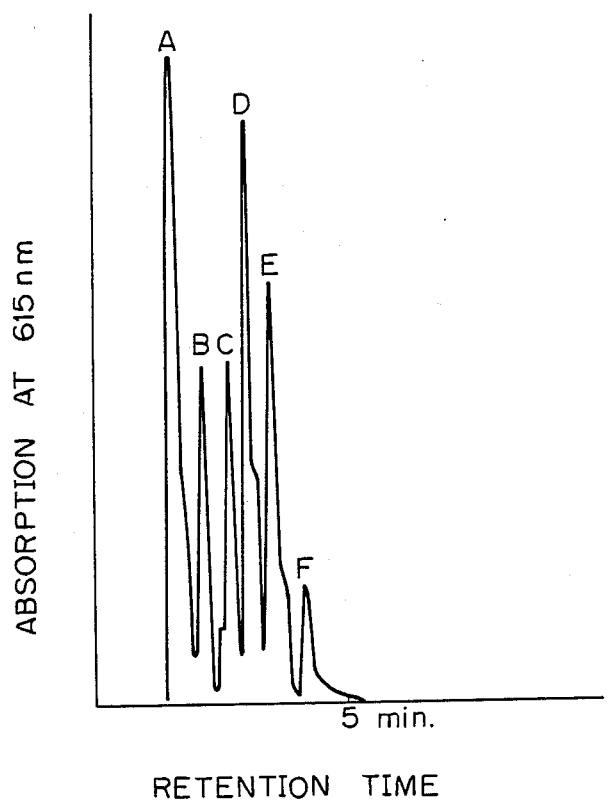
FIG. 1 is a high-pressure liquid chromatogram showing a typical example of the chemistry of the blue dye composition of the present invention.

The highly stable blue dye composition of the present invention, when analyzed by high-pressure chromatography on a YMC ODS A-312 of Yamamura Kagaku Kenkyusho which comprises spherical and porous silica particles (particle size, 5 μm; pore size, 120 Å; column diameter, 0.6 cm; column length, 15 cm; solvent, 60% methanol at 1 ml/min.; detector, spectrophotometer at 615 nm), typically produces a chromatogram of the profile shown in FIG. 1, revealing that the composition is a mixture with six principal components A to F. The retention times of the respective components A to F are: ca. 1.6 min., ca. 2.3 min., ca. 2.7 min., ca. 2.9 min., ca. 3.6 min. and ca. 4.4 min. Visible absorption spectra of components A to F in their isolated forms obtained by conducting high-pressure liquid chromatography under the same conditions as shown above yield the following data: A, B and C each having an absorption maximum ($\lambda_{max}$) at 592 nm afford a brilliant bluish purple color; E and F having $\lambda_{max}$ values of ca. 614 nm and ca. 627 nm impart a brilliant blue color; and D has $\lambda_{max}$ of 602 nm.

In order to produce the blue dye composition of the present invention, genipin and 0.5–2.0 equivalents of taurine are added to a buffer solution that will not be involved in reaction, and the mixture is heated for 2–20 hours. The concentration of genipin used in this reaction is in the range of 5–20 mmol/l. Any buffer solution can be used so long as it will not take part in the reaction. The heating temperature is generally in the range of 40–100° C., most preferably at ca. 80° C., and reaction may be accomplished by shaking, agitation, aeration or any other suitable action.

The proportions of components A to F in the blue dye composition of the present invention can be varied by adjusting the pH employed in carrying out the invention. If the reaction is performed at pH 7–9, most preferably at ca. 8, a dye composition that is chiefly composed of component A and which generally affords a bluish purple color will result. The reaction for producing this composition is generally continued for 2–20 hours, preferably 8–10 hours, with temperature and other conditions being the same as specified in the preceding paragraph. The bluish purple dye composition thus obtained typically produces a visible absorption spectrum ($\lambda_{max}$, 592 nm; half-width, 80 nm) in an aqueous solution of 40% ethanol. Analysis by high-pressure liquid chromatography (hereinafter abbreviated as HPLC) under the conditions already mentioned shows that at least 80% of this composition is composed of component A having a retention time (hereinafter RT) of 1.6 min. Although the structure of component A has yet to be identified, the composition has good stability characteristics (e.g. high resistance to heat, changes in pH, and alcohol) and affords a brilliant bluish purple color.

If the reaction between genipin and taurine is carried out at a pH of 4–7, preferably at ca. 6, a blue dye composition that has a more uniform distribution of all components A to F and which imparts a somewhat dark tone will result. The reaction for producing this composition is generally continued for 2–10 hours, preferably 3–5 hours, under the conditions already specified. The blue dye composition thus produced has superior resistance to heat, changes in pH and alcohol and may be immediately put to use in certain applications If desired, a brighter blue dye composition can be produced by performing the following fractionating procedures.

The starting blue dye composition is dissolved in an aqueous solvent, such as water or a mixture of alcohol and water, and the solution is passed through a column packed with a highly porous resin; after washing the column with water, any unwanted components are eluted with 10–30% ethanol, preferably ca. 16% ethanol, followed by eluting a desired blue dye with 80–100% ethanol, preferably 95% ethanol. The highly porous resin to be used is not limited to any particular type, but either Diaion HP-20 resin or its equivalent, Amberlite XAD-2 resin, is the preferred resin for use in the column. Diaion HP-20 (a product of Mitsubishi Chemical Industries, Ltd., Tokyo, Japan) is a highly porous, synthetic adsorbent with a specific surface area of 718.0 m$^2$/g and a pore volume of 1.16 ml/g, consisting of styrene and divinylbenzene copolymer in bead form of a macroreticular structure. Use of the HP-20 resin is most preferable, but its functional equivalent, Amberlite XAD-2 resin (a product of Rohm and Haas, Philadelphia, PA) is also acceptable. XAD-2 resin is also a highly porous, synthetic adsorbent with a specific surface area of 300 (m$^2$/g-dry basis) and a porosity of 0.42 (ml pore/ml bead-dry basis), consisting of styrene and divinylbenzene copolymer in bead form. The resin is used in an amount of 0.1–5 l, preferably 0.5–1 l, for 1 g of the genipin used in the reaction. The amounts of washing water and eluant may vary depending upon such factors as the amount of resin used, the composition of eluant, and the rate of elution.

The fractions obtained by elution with 95% ethanol are combined and concentrated under vacuum to produce a solution containing a desired brighter blue dye composition. This composition has good stability characteristic (e.g. high resistance to heat, changes in pH( and alcohol) and HPLC conducted under the conditions already specified shows that it is chiefly composed of component E with RT of 3.6 min. and that it affords a brilliant blue color.

In producing the blue dye composition of the present invention, the starting genipin may be the crude product that is obtained by hydrolyzing the gardenia fruit derived iridoid glycoside mixture with β-glucosidase.

As will be shown later in Example 2, the blue dye composition of the present invention thus produced by the method described above is far stabler than the prior art natural blue dye and hence is particularly suitable for use as a colorant in foods or drugs. The composition may be used either after appropriately concentrating or diluting the solution as obtained by the process described above, or if desired, after drying the solution into a powder state. Depending on the specific object of use, the so prepared dye composition, either alone or in admixture with another dye, may be used as a colorant in a broad range of applications including foods and drugs.

The following examples are provided for the purpose of further illustrating the present invention but are in no sense to be taken as limiting.

EXAMPLE 1

Genipin (2.25 g) and taurine (1.88 g) were dissolved in 400 ml of a weakly alkaline (pH 8.0) MacIlvain's buffer solution and the mixture was shaken at 80° C. for 9 hours. MacIlvain's buffer (disclosed in T. C. MacIlvain, *J. Biol. Chem.*, 49,183 (1921)) is characterized by a pH value ranging from 2.2 to 8.0 by appropriate combination of 0.2M Na$_2$HPO$_4$ and 0.1M citric acid. The resulting dye solution (400 ml) was a solution containing a bluish purple dye composition that had an absorption maximum ($\lambda_{max}$) of 592 nm (in 40% ethanol), absorbance of 144 and a half-width of 80 nm in visible absorption spectrum. The dye composition contained component A in an amount of at least 80%.

EXAMPLE 2

Genipin (2.25 g) and taurine (1.25 g) were dissolved in 400 ml of a weakly acidic (pH 6.0) MacIlvain's buffer solution and the mixture was shaken at 80° C. for 4 hours. The resulting dye solution was a solution containing a blue dye composition that had $\lambda_{max}$ of 595 nm (in 40% ethanol), absorbance of 113 and a half-width of 100 nm. Analysis of the dye solution by HPLC under the conditions already specified showed that it was composed of six components A to F having the already indicated retention times (see FIG. 1).

Figure 2:
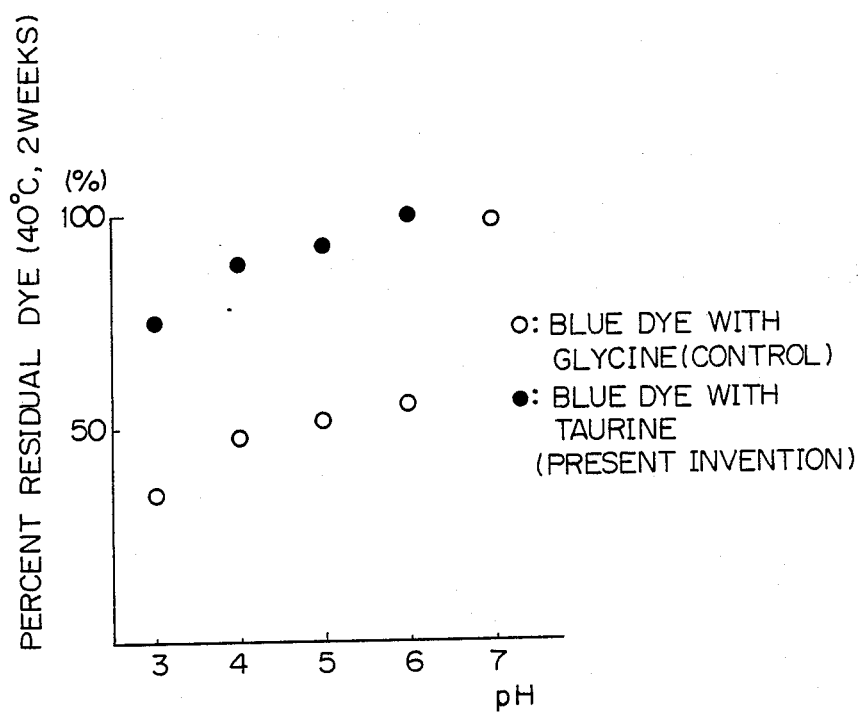
FIG. 2 is a graph illustrating the stability of the blue dye composition of the present invention in an aqueous solution.

A comparative sample of blue dye composition was prepared by reacting genipin with glycine in accordance with the method described in Japanese Patent Public Disclosure No. 13451/1979, and the stability of this sample was compared with that of the dye composition prepared in Example 2. Aqueous solutions of each composition having substantially the same concentration but different pHs were prepared; these solutions were left indoors at 40° C. for 2 weeks and the residual dye contents were measured with a spectrophotometer in terms of absorbance at absorption maxima in the visible range of the spectrum. The results are shown in FIG. 2. The composition of the present invention experienced a negligible drop in dye concentration at pH 6.0 and its residual dye content at pH 3.0 was higher than the value for the comparative composition.

EXAMPLE 3

Genipin (27.12 g) was dissolved in 500 ml of water. After dissolving 11.3 g of taurine, 1 N NaOH was slowly added to the solution to adjust its pH to 5.5. The solution was then shaken at 80° C. for 4 hours to obtain a solution containing a blue dye composition. The composition has $\lambda_{max}$ of 593 nm (in 40% ethanol), absorbance of 1,400 and a half-width of 96 nm. Analysis by HPLC showed that this composition contained components A to F in substantially the same proportions as in the composition prepared in Example 2.

EXAMPLE 4

Fifty milliliters of the solution prepared in Example 3 which contained a blue dye composition was passed through a column (10 cm$^\phi \times$20 cm$^L$) packed with 1.6 liters of a highly porous polymer resin HP-20 (Mitsubishi Chemical Industries Limited). Elution was conducted by successively passing water (3.2 l), 16% ethanol (3.2 l) and 95% ethanol (2.4 l). The appropriate fractions (eluted with 95% ethanol) were combined and concentrated under vacuum to obtain 400 ml of a solution containing a bright blue dye composition. This composition has $\lambda_{max}$ of 606 nm (in 40% ethanol), absorbance of 290 and a half-width of 70 nm. Analysis by HPLC showed that the composition prepared in Example 4 was chiefly composed of component E.

EXAMPLE 5

One kilogram of the dried fruit of gardenia was ground into particles and leached with 10 liters of water. Two-hundred milliliters of the resulting yellow dye solution was mixed with 100 ml of the solution prepared in Example 4 which contained a bright blue dye composition. As a result, a solution of colorant based on green dye was obtained. Six milliliters of this solution was added to 100 ml of 40% ethanol to produce a solution affording a bright green color.

EXAMPLE 6

Two kilograms of a dried orange peel was reconstituted with water, immersed in 10 liters of stock alcohol and distilled. To 420 ml of the distillate (alcoholic content: 95% v/v) were added 300 g of fine granulated sugar, 100 ml of tap water, and 15 ml of the solution prepared in Example 4 which contained a bright blue dye. As a result, blue curacao with a brilliant blue color was obtained. The blue color of this liqueur was very stable.

What is claimed is:

1. A blue dye composition that is prepared by reacting genipin with taurine at a temperature between 40 and 100° C. and at a pH between 4 and 9 and which, when analyzed by high-pressure chromatography, produces a chromatogram containing the following six principal components, A to F, which respectively have approximate retention times of 1.6 min., 2.3 min., 2.7 min., 2.9 min., 3.6 min., and 4.4 min., with components A, B and C each having an absorption maximum ($\lambda_{max}$) of about 592 nm, component D with $\lambda_{max}$ of about 602 nm, component E with $\lambda_{max}$ of about 614 nm, and component F with $\lambda_{max}$ of about 627 nm, as measured in 40% ethanol.

2. A composition according to claim 1 which is prepared by reacting genipin with taurine at about pH 8 and contains component A in an amount of at least 80%, and generally assumes a bluish purple color.

3. A composition according to claim 1 which is prepared by reacting genipin with taurine at about pH 6 and contains component A in an amount of no more than 50%, and assumes a blue color.

4. A composition according to claim 1 which is prepared by fractionation of the composition of claim 3 and is chiefly composed of component E, and assumes a bright blue color wherein the fractionation is performed using an adsorption resin of styrene and divinylbenzene copolymer selected from Amberlite XAD-2, Dialon HP-20 or an equivalent thereof.

5. A colorant which is composed of a blue dye composition or a mixture thereof with another dye, the improvement comprising that said composition is prepared by reacting genipin with taurine at a temperature between 40 and 100° C. and at a pH between 4 and 9 and which, when analyzed by high-pressure chromatography, produces a chromatogram containing the following six principal components, A to F, which respectively have approximate retention times of 1.6 min., 2.3 min., 2.7 min., 2.9 min., 3.6 min., and 4.4 min., with components A, B and C each having an absorption maximum ($\lambda_{max}$) of about 592 nm, component D with $\lambda_{max}$ of about 602 nm, component E with $\lambda_{max}$ of about 614 nm, and component F with $\lambda_{max}$ of about 627 nm, as measured in 40% ethanol.

* * * * *